(12) United States Patent
Nistico et al.

(10) Patent No.: US 9,107,622 B2
(45) Date of Patent: Aug. 18, 2015

(54) OPTICAL MEASURING DEVICE AND SYSTEM

(75) Inventors: Walter Nistico, Berlin (DE); Jan Hoffmann, Berlin (DE); Eberhard Schmidt, Kleinmachnow (DE)

(73) Assignee: SENSOMOTORIC INSTRUMENTS GESELLSCHAFT FUR INNOVATIVE SENSORIK MBH, Teltow (DE)

( * ) Notice: Subject to any disclaimer, the term of this patent is extended or adjusted under 35 U.S.C. 154(b) by 0 days.

(21) Appl. No.: 14/005,295
(22) PCT Filed: Mar. 15, 2012
(86) PCT No.: PCT/EP2012/054607
§ 371 (c)(1),
(2), (4) Date: Nov. 14, 2013
(87) PCT Pub. No.: WO2012/126809
PCT Pub. Date: Sep. 27, 2012

(65) Prior Publication Data
US 2014/0055746 A1    Feb. 27, 2014

(30) Foreign Application Priority Data

Mar. 18, 2011  (EP) .................................... 11158891
Jul. 13, 2011  (EP) .................................... 11173755

(51) Int. Cl.
| | | |
|---|---|---|
| A61B 3/14 | (2006.01) | |
| A61B 3/00 | (2006.01) | |
| A61B 3/024 | (2006.01) | |
| A61B 3/11 | (2006.01) | |
| A61B 3/113 | (2006.01) | |
| G02B 27/00 | (2006.01) | |

(Continued)

(52) U.S. Cl.
CPC .................. *A61B 3/14* (2013.01); *A61B 3/0008* (2013.01); *A61B 3/024* (2013.01); *A61B 3/112* (2013.01);
(Continued)

(58) Field of Classification Search
CPC ...... A61B 3/12; A61B 3/1208; A61B 3/1216; A61B 3/1225; A61B 3/1233; A61B 3/1241; A61B 3/14; A61B 3/15; A61B 3/152; A61B 3/18

USPC .......................................... 351/205–210, 213
See application file for complete search history.

(56) References Cited

U.S. PATENT DOCUMENTS

| | | | |
|---|---|---|---|
| 4,145,122 A | 3/1979 | Rinard et al. | |
| 4,300,818 A | 11/1981 | Schachar | |

(Continued)

FOREIGN PATENT DOCUMENTS

| | | |
|---|---|---|
| CN | 101238497 A | 8/2008 |
| CN | 101356468 A | 1/2009 |

(Continued)

OTHER PUBLICATIONS

Communication dated Mar. 30, 2015, from the State Intellectual Property Office of People's Republic of China in counterpart Application No. 201280013861.2.

*Primary Examiner* — Scott J Sugarman
*Assistant Examiner* — William R Alexander
(74) *Attorney, Agent, or Firm* — Sughrue Mion, PLLC (57) ABSTRACT

The invention relates to an optical measuring device (1) for capturing at least one parameter of at least one eye (10*l*, 10*r*) of a test person (31) wearing the optical measuring device (1), comprising a frame (4), at least one frame insert (8*l*, 8*r*) attached to the frame (4) and at least one capturing unit (3*l*, 3*r*), wherein the frame (4) is designed to fix the optical measuring device (1) in such a way to the head of the test person (31), that the at least one frame insert (8*l*, 8*r*) is positioned in front of at least one eye (10*l*, 10*r*) of the test person (31) for at least one direction of view of the at least one eye (10*l*, 10*r*) on the optical axis (K) of the at least one eye (10*l*, 10*r*), and the capturing unit (3*l*, 3*r*) is designed to optically capture the at least one parameter of the at least one eye (10*l*, 10*r*), wherein the capturing unit (3*l*, 3*r*) is arranged in such a way (a) that the optical path (M) for the capturing of the at least one parameter of the at least one eye (10*l*, 10*r*) excludes the frame insert (8*l*, 8*r*).

17 Claims, 10 Drawing Sheets

(51) Int. Cl.
  *G02B 27/01* (2006.01)
  *G06F 3/01* (2006.01)
  *A61B 3/107* (2006.01)

(52) U.S. Cl.
  CPC ............ *A61B 3/113* (2013.01); *G02B 27/0093* (2013.01); *G02B 27/017* (2013.01); *G06F 3/013* (2013.01); *A61B 3/107* (2013.01); *G02B 2027/014* (2013.01); *G02B 2027/0138* (2013.01); *G02B 2027/0178* (2013.01); *G02B 2027/0187* (2013.01)

(56) References Cited

U.S. PATENT DOCUMENTS

| | | |
|---|---|---|
| 5,861,936 A | 1/1999 | Sorensen |
| 6,163,281 A | 12/2000 | Torch |
| RE39,539 E | 4/2007 | Torch |
| 7,515,054 B2 * | 4/2009 | Torch .................. 340/573.1 |
| 2002/0036750 A1 * | 3/2002 | Eberl et al. ............... 351/207 |
| 2002/0101568 A1 * | 8/2002 | Eberl et al. ............... 351/211 |
| 2004/0196433 A1 | 10/2004 | Durnell |
| 2009/0244485 A1 * | 10/2009 | Walsh et al. .............. 351/221 |
| 2010/0134761 A1 | 6/2010 | Johns et al. |
| 2010/0220291 A1 | 9/2010 | Horning et al. |

FOREIGN PATENT DOCUMENTS

| | | |
|---|---|---|
| WO | 99/67757 A1 | 12/1999 |
| WO | 2004/066097 A2 | 8/2004 |
| WO | 2005094667 A2 | 10/2005 |
| WO | 2006/011870 A1 | 2/2006 |
| WO | 2010/083853 A1 | 7/2010 |

* cited by examiner

OPTICAL MEASURING DEVICE AND SYSTEM

The invention relates to an optical measuring device for capturing at least one parameter of at least one eye of a test person wearing the optical measuring device, comprising a frame, at least one frame insert attached to the frame and at least one capturing unit, wherein the frame is designed to fix the optical measuring device in such a way to the head of the test person, that the at least one frame insert is positioned in front of the at least one eye of the test person for at least one direction of view of the at least one eye on the optical axis of the at least one eye, and the capturing unit is designed to optically capture the at least one parameter of the at least one eye. The invention also relates to a system comprising such an optical measuring device.

It is known from the prior art to use head mounted eye tracker devices. U.S. Pat. No. RE39,539 E discloses an apparatus for monitoring movement of a person's eye. The system includes a frame that is worn on a person's head, an array of emitters on the frame for directing light towards the person's eye, and an array of sensors on the frame for detecting light from the array of emitters. The sensors detect light that is reflected off of respective portions of the eye or its eyelid, thereby producing output signals indicating when the reflective portion of the eye is covered by the eyelid. The system allows to monitor the persons level of drowsiness.

U.S. Pat. No. 6,163,281 discloses a system and method for communication using movement of a person's eye, including an emitter for directing light towards an eye, a sensor for detecting emitted light from the emitter, and a processor coupled to the sensor for converting sequential light intensity signals received from the sensor to a stream of data, and/or for converting the signals into an understandable message.

US 2004/0196433 A1 discloses an eye tracking system for monitoring the movement of a user's eye comprising an eye camera and a scene camera for supplying to interlace electronics video data indicative of an image of the user's eye and an image of the scene observed by the user. In addition, the system incorporates a frame grabber for digitizing the video data and for separating the eye and scene data into two processing channels, and a spot location module for determining from the video data the location of a reference spot formed on the user's eye by illumination of the user's eye by a point source of light. The system further incorporates a pupil location module in order to determine the user's line of gaze.

WO 2010/83853 A1 discloses a gaze point detection system with one or more infrared signal sources to be placed in a test scene as reference points, at least one pair of eye glasses worn by a test subject, and a data processing and storage unit for calculating a gaze point of the person. The eye glasses comprise an image sensor adapted to detect IR signals from the at least one IR signal source and to generate an IR signal source tracking signal, an eye tracking unit adapted to determine the gaze direction of the test subject person and to generate an eye tracking signal, and a camera unit adapted to acquire a test scene picture.

WO 2004/066097 A2 discloses an eye tracking system for displaying a video screen pointer at a point of regard of a users gaze. The system comprises a camera focused on the user's eye, a support connected to the camera for fixing the relative position of the camera to the user's pupil, and a computer having a CPU and an eye tracking interface. By determining the center of the eye, a pointer on the video display screen can be displayed at the point of regard. WO 2004/066097 A2 discloses an optical measuring device according to the preamble of the present application.

US 2010/0220291 A1 discloses an eye tracking system with a transparent lens, at least one light source, and a plurality of light detectors. The transparent lens is adapted for disposal adjacent an eye. At least one light source is disposed within the transparent lens and is configured to emit light towards the eye. The at least one light source is transparent to visible light. The plurality of light detectors is disposed within the transparent lens and is configured to receive light that is emitted from the at least one light source and is reflected off of the eye. Each of the light detectors is transparent to visible light and is configured, upon receipt of light that is reflected off of the eye, to supply an output signal.

Known head mounted eye trackers suffer from the disadvantage that environmental stray light being reflected on the test person's eye may negatively influence the eye tracking functionality. Cameras monitoring the test person's eyes may not be able to distinguish between features of the eyes explicitly used for keeping track of the eye movement and features, such as reflections, arising from environmental lighting conditions. In general, the illumination situation is not very well defined. Reliable eye tracking is often compromised by environmental conditions and undesired stray light disturbing the tracking mechanism. Thus, known head mounted eye tracker devices usually suffer from a limited accuracy and robustness. To improve detection accuracy, time consuming and difficult calibration procedures are required.

An object of the present invention is to provide an optical measuring device and a system which allow for a more reliable capturing of at least one parameter characterizing an eye.

This task according to the invention is solved by an optical measuring device having the features according to patent claim 1 and a system having the features according to patent claim 15. Advantageous embodiments of the invention are the subject matter of the independent claims and the description.

The optical measuring device according to the invention serves for capturing at least one parameter of at least one eye of a test person wearing the optical measuring device. The optical measuring device comprises a frame, at least one frame insert attached to the frame and at least one capturing unit, wherein the frame is designed to fix the optical measuring device in such a way to the head of the test person that the at least one frame insert is positioned in front of the at least one eye of the test person for at least one direction of view of the at least one eye on the optical axis of the at least one eye, and the capturing unit is designed to optically capture the at least one parameter of the at least one eye. The capturing unit of the optical measuring device is arranged in such a way that the optical path for the capturing of the at least one parameter of the at least one eye excludes the frame insert.

This way, frame insert and capturing unit are optically decoupled. Both elements can serve for different purposes without having to provide an interrelated functionality. In particular, the optical path of the capturing unit is neither directed through the frame insert nor does it include the surface of the frame insert as a reflective optical element. Thus, the optical properties of the frame insert can be designed without having to take the requirements for the optical path into consideration. This way, new optical design options can be offered which allow a more reliable and efficient capturing of the at least one parameter of the eye. The optical path of the capturing unit is not deteriorated by the frame insert.

The frame insert can be any element which can be inserted and/or attached to the frame of the optical measuring device. It can either be transparent or non-transparent. The frame insert can be any element distinct from the frame (e.g. due to its material) which is fixed to the frame or can be attached to it. The capturing unit may comprise at least one camera. In particular, the optical axis of the at least one eye can be the gaze direction of the eye. The optical path or detection path of the capturing unit excludes the frame insert, i.e. the frame insert is not part of the optical path of the capturing unit. If the optical path is described in terms of geometrical optics particularly no light ray characterizing the optical path has a common point with the frame insert.

Advantageously, the frame insert is arranged in such a way that, with the optical measuring device fixed to the head of the test person, through a connection line of a point of the frame insert with the eye of the test person a view path is determined, and the capturing unit is arranged in such a way that the optical path for capturing the at least one parameter of the eye and the view path as single jointly used optical element comprise the eye. In particular, the frame insert is explicitly not an optical element used jointly by the eye as well as by the capturing unit. Specifically, this embodiment is to be understood in terms of ray optics. In particular, the test person's line of sight is directed onto or through the frame insert, while this line of sight and the line of sight of the capturing unit are entirely decoupled by not using a common optical element. This embodiment guarantees that the frame insert is solely used for influencing the test person's view by affecting its line of sight. On the other hand, with the capturing unit the eye can be directly observed while not being negatively influenced by the optical characteristics of the frame insert.

Advantageously, the optical path entirely runs within a space which with the optical measuring device fixed to the head of a test person extends on the side of the frame insert facing the at least one eye. This way, the optical path of the capturing unit can be properly shielded by the frame insert. Depending on the characteristics of the frame insert the quality for capturing the at least one parameter of the eye can be significantly improved. Specifically, the frame insert can block undesired light from the space which the optical path extends through. Unwanted reflections and stray light can be prevented from reaching the capturing unit by the frame insert.

Advantageously, the at least one frame insert has at least one optical property. In particular, the at least one frame insert can be configured as an optical element, in particular as an optical lens and/or a diffractive optical element. In particular, the frame insert can comprise at least one eye glass lens. This way, the frame insert may improve the test person's optical perception of the environment. The line of sight of the test person may be improved. On the other hand, the optical property of the frame insert can be chosen such that the quality for capturing the at least one parameter by the capturing unit is improved.

In one embodiment this can be achieved such that at least one frame insert in the visible spectral range at least over a wavelength range is optically configured as neutral density filter. A neutral density filter reduces light intensity over a broad wavelength range, especially in the visible spectrum. This way, the pupil of the eye may become wider despite unchanged illumination conditions in the environment. If the captured parameter of the eye is the pupil diameter, larger pupil diameters usually guarantee for improved and more reliable detection by the capturing unit. The frame insert comprising a neutral density filter consequently improves the detection quality achievable with the capturing unit. Furthermore, overexposure of the captured image can be avoided yielding better image quality.

In another embodiment the at least one frame insert is configured as optical spectral filter, in particular as high pass filter, low pass filter, band pass filter, or Notch filter. Such filters guarantee that only light of a specific spectral range can reach the eye behind the frame insert. Thus, light which negatively influences the capturing capabilities of the capturing unit can explicitly be blocked. Unwanted reflections on the eye and undesirable stray light in a specific wavelength range can thus be prevented. The capturing quality of the at least one parameter is very high.

Preferentially, the capturing unit at least in one pre-determinable spectral range is optically sensitive. In particular, this spectral range is pre-determined such that it is correlated with the optical properties of the at least one frame insert. For instance, the capturing unit can be designed such that it is optically sensitive in a spectral range that is blocked by the frame insert. Light passing through the frame insert can consequently not negatively influence the capturing capabilities of the capturing unit. A complete optical decoupling is achieved. For the capturing unit a darkened space behind the frame insert is created thus providing for nearly background free capturing of the parameter of the eye. Particularly, the properties of the frame insert and the capturing unit can be chosen such that the frame insert is nearly completely transparent in the visible wavelength range thus allowing for an unobstructed view of the environment, and nearly completely opaque in a wavelength range in which the capturing unit is optically sensitive.

Advantageously, the optical measuring device comprises at least one illumination unit which with the optical measuring device fixed to the head of the test person is configured to emit radiation in the pre-determinable spectral range in such a way that the radiation at least partly hits the at least one eye. The illumination unit can then illuminate the eye with light that can be captured by the capturing unit. Specific reflections and/or illumination patterns (structured illumination) can be generated on the eye which can help the capturing unit in capturing the at least one parameter. In a preferred embodiment, the features of the frame insert being configured as an optical spectral filter, the capturing unit being optically sensitive in the pre-determinable spectral range, and the illumination unit emitting light in the pre-determined spectral range are combined. The optical spectral filter of the frame insert is then preferentially designed such that it is at least partly opaque in the pre-determinable spectral range for which the capturing unit and the illumination unit are optimized. Preferentially, the at least one frame insert in the pre-determinable spectral range has a transmittance of less than 40%, preferentially less than 20%. Then, a completely different light environment behind the frame insert can be created, which allows for optimized capturing of the at least one parameter by the capturing unit. The optically decoupled situation improves capturing and detection efficiency.

In one embodiment the illumination unit and the frame insert are configured in such a way that the pre-determinable spectral range for the radiation emission of the illumination unit and the pre-determinable spectral range in which the frame insert is essentially opaque are changeable in a correlated fashion. The detection scheme can then be adjusted to the illumination conditions in the environment.

Advantageously, the at least one frame insert at least partly has a reflection coefficient larger than 40%, preferentially larger than 60%, in the pre-determinable spectral range. This way, background light potentially disturbing the capturing process is sufficiently suppressed.

In a preferred embodiment the pre-determinable spectral range is in the infrared wavelength range. Then, the frame insert can be transparent in a visible spectral range while mainly blocking infrared light. As the human eye is not sensitive to infrared light the frame insert would thus appear entirely transparent to the test person and not obstruct his vision. On the other hand, an IR stray light free environment behind the frame insert would be created for efficient capturing of desired reflections created on the eye of the test person by an infrared illumination unit.

Advantageously, the capturing unit is arranged in such a way on the frame that with the optical measuring device fixed to the head of the test person the optical path capturing the at least one parameter of the at least one eye extends in a straight line from the capturing unit to the eye. In particular, the optical path does not contain any optical elements, especially no reflecting optical elements. The capturing unit can then observe the eye directly without interference from optical elements.

Alternatively, the optical measuring device can comprise an optical deflection element, the optical deflection element and the capturing unit being arranged in such a way on the frame that with the optical measuring device fixed to the head of the test person the optical path for capturing the at least one parameter of the at least one eye extends from the capturing unit via the deflection element to the eye. By re-directing the optical path many different possibilities for positioning the capturing unit on the optical measuring device exist. A highly integrated and compact measuring device is realized. The optical path can be adjusted by aligning the deflection element without having to change the position of the capturing unit. Capturing units with a low numerical aperture can be used.

Advantageously, the optical measuring device is configured in such a way that, when fixed to the head of the test person wearing eye glasses the at least one frame insert is positioned in front of at least one eye glass lens of the eye glasses of the test person. The optical measuring device can then be worn by a test person which needs corrective eye glasses to improve its vision.

Advantageously, the frame insert is configured as a multipart element comprising at least one carrier element and at least one optical element, wherein in particular the optical element interacts with the capturing unit in such a way that it allows for the capturing unit to optically capture the at least one parameter of the at least one eye and/or supports it in doing so. In particular, the optical element can be reflective in a wavelength range the capturing unit is sensitive to. Advantageously, the at least one optical element is configured as mirror and/or reflective coating. In particular, the carrier element can be a transparent eye glass, while the optical element may be a reflective coating on the eye glass.

Advantageously, the at least one captured parameter concerns an orientation and/or a position and/or an eyelid closure and/or a pupil diameter and/or limbus characteristic and/or a sclera characteristic and/or an iris characteristic and/or a characteristic of a blood vessel and/or a cornea characteristic of the at least one eye. In particular the at least one captured parameter may concern a cornea radius (anterior, posterior), an eyeball radius, a distance pupil-center to cornea-center, a distance cornea-center to eyeball-center, a distance pupil-center to limbus center, a cornea keratometric index of refraction, a cornea index of refraction, a vitreous humor index of refraction, a distance crystalline lens to eyeball-center and to cornea center and to corneal apex, a crystalline lens index of refraction, a visual axis orientation, an optical axis orientation, a pupil axis (achromatic axis) orientation, a line of sight orientation, an astigmatism degree (diopters) and orientation angle of flat and steep axis, an iris diameter, pupil diameters (pupil major and minor axes), pupil area), limbus major and minor axes, eye cyclo-torsion, eye intra-ocular distance, eye vergence, statistics over eye adduction/abduction and statistics over eye elevation/depression. The optical measuring device can then work as an eye tracking device.

Advantageously, the frame insert comprises a display unit. The display unit can be transparent, partly transparent or opaque.

Advantageously, with the optical measuring device fixed to the head of the test person a display on the display unit is optically capturable by at least one eye of the test person. This embodiment allows to capture the at least one parameter of the eye of the test person, while the test person is watching a specific display on the display unit. While specific information is being displayed, the capturing unit is not negatively influenced by the display as the optical path for the capturing of the at least on parameter excludes the display unit. Optical decoupling allows for an unobstructed observation of the eyes by the capturing unit. The capturing unit exclusively captures information concerning the eye of the test person and not information being displayed on the display unit.

The optical measuring device can be a spectacle device.

A system according to the invention comprises an optical measuring device according to the invention and at least two frame inserts which differ in their transmission and/or reflection properties, wherein the frame is configured in such a way that the at least two frame inserts are exchangeably attachable to it. Depending on the measuring conditions and/or light conditions in the environment, suitable frame inserts for optimum capturing capabilities of the capturing unit can be chosen. Reconfiguration of the system by exchange of a frame insert can be easily accomplished by the test person itself. The optical measuring device can then be flexibly adjusted to changing conditions. In a variety of conditions, very good capturing capabilities of the optical measuring device can be achieved.

In one aspect of the invention, a method is concerned that allows to exchange different frame inserts in an optical measuring device. In a first configuration of a system comprising an optical measuring device and at least two frame inserts, a first frame insert of the at least two frame inserts is attached to a frame of the optical measuring device. The first frame insert has a first transmission characteristic. When environmental lighting conditions change, a second frame insert of the at least two frame inserts becomes more suitable for the changed lighting condition, as its use principally improves the capturing of at least one parameter of at least one eye of a test person. According to a step of the method the test person may now choose the second frame insert, remove the first frame insert from the frame of the optical measuring device and exchange it for the second frame insert. The second frame insert becomes then attached to the frame and the capturing capabilities under the changed lighting conditions are improved. The optical measuring device can be flexibly adjusted to changing environmental lighting conditions. Alternatively, different frame inserts may be used for different capturing functional principles of the optical measuring device.

Another aspect of the invention concerns a spectacle device for capturing at least one parameter of at least one eye of a test person wearing the spectacle device, the spectacle device comprising a frame, at least one frame insert attached to the frame, and at least one capturing unit, wherein the frame is configured to fix the spectacle device to the head of the test person in such a way that the at least one frame insert is positioned in front of at least one eye of the test person for at least one direction of view of the eye on the optical axis of the eye, and the capturing unit is configured to optically capture the at least one parameter of the at least one eye, wherein the frame insert comprises a display unit.

Advantageously, with the spectacle device fixed to the head of the test person a display on the display unit is optically capturable by the at least one eye of the test person.

Advantageously, the frame insert of the spectacle device comprises an eyeglass lens.

Advantageous embodiments of the optical measuring device according to the present invention are also to be considered advantageous embodiments of the system according to the invention and the spectacle device according to the further aspect.

Further features of the invention derive from the claims, the figures, and the description of the figures. All features and feature combinations previously mentioned in the description as well as the features and feature combinations mentioned further along in the description of the figures and/or shown solely in the figures are not only usable in the combination indicated in each case, but also in different combinations or on their own.

The invention is now explained in more detail with reference to individual preferred embodiments and with reference to the attached drawings. These show in.

Figure 2:
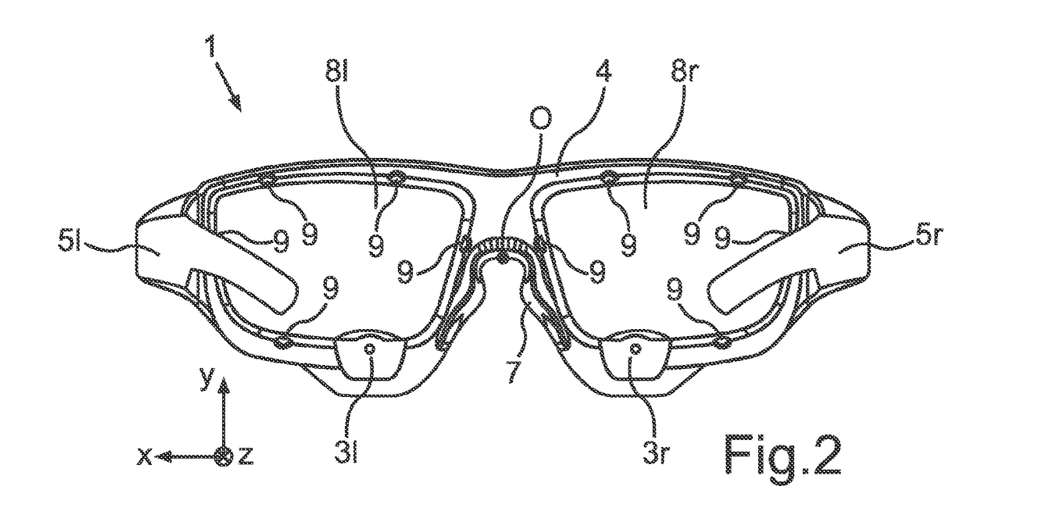
FIG. 2 a rear view of a spectacle device.
Figure 3:
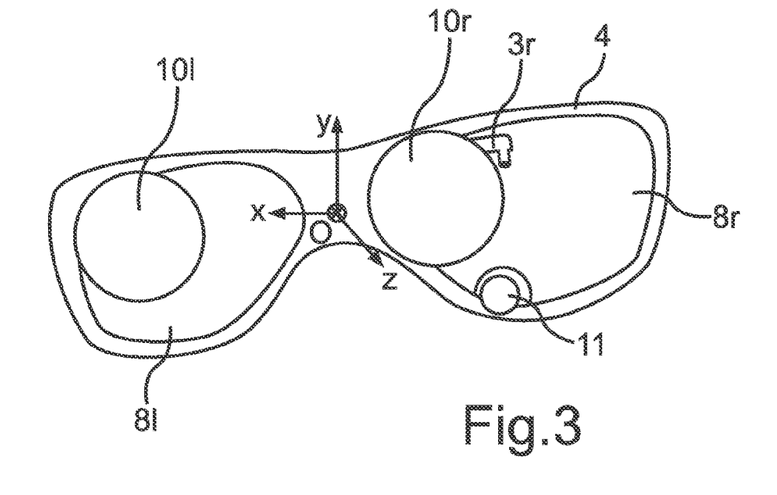
FIG. 3 a schematic rear view of a spectacle device with an eye camera making use of a deflection element to direct its optical path onto the eye.
Figure 4:
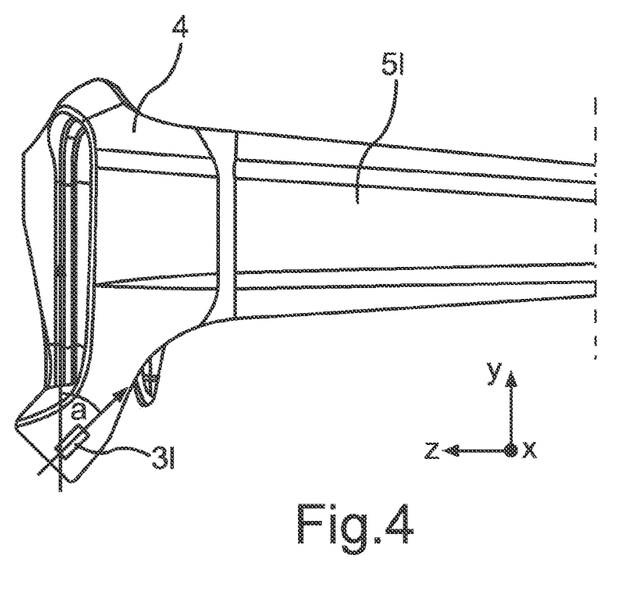
FIG. 4 a side view of a spectacle device schematically showing the orientation of an eye camera.

In the figures same elements or elements of the same function are equipped with the same reference signs. FIGS. 2, 3, and 4 show the same reference frame with a Cartesian coordinate system and perpendicular axes x, y and z.

Figure 1A:
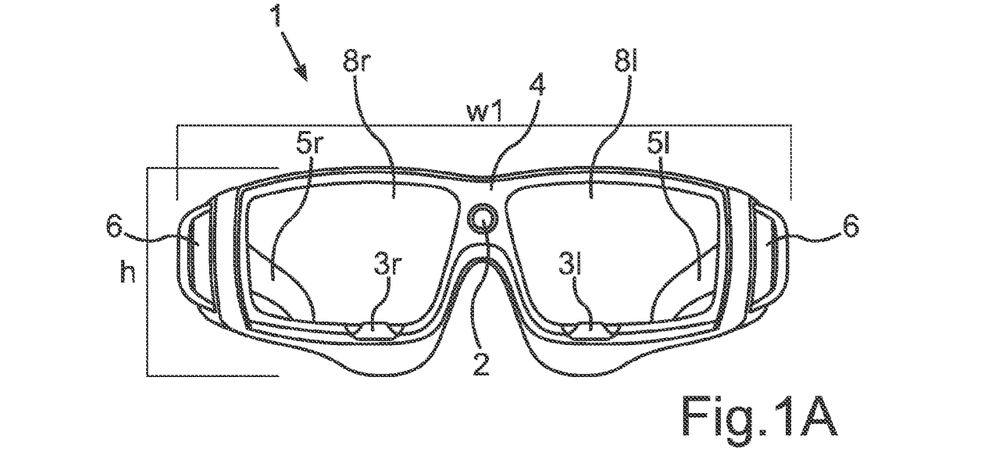
FIG. 1A a front view of a spectacle device according to an embodiment of the invention.
Figure 1B:
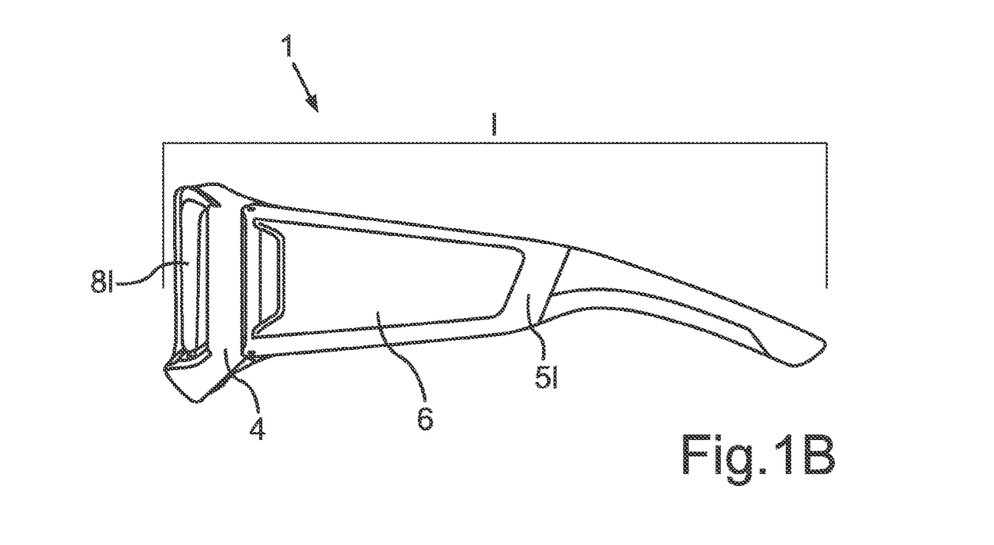
FIG. 1B a side view of the spectacle device of FIG. 1A.
Figure 1C:
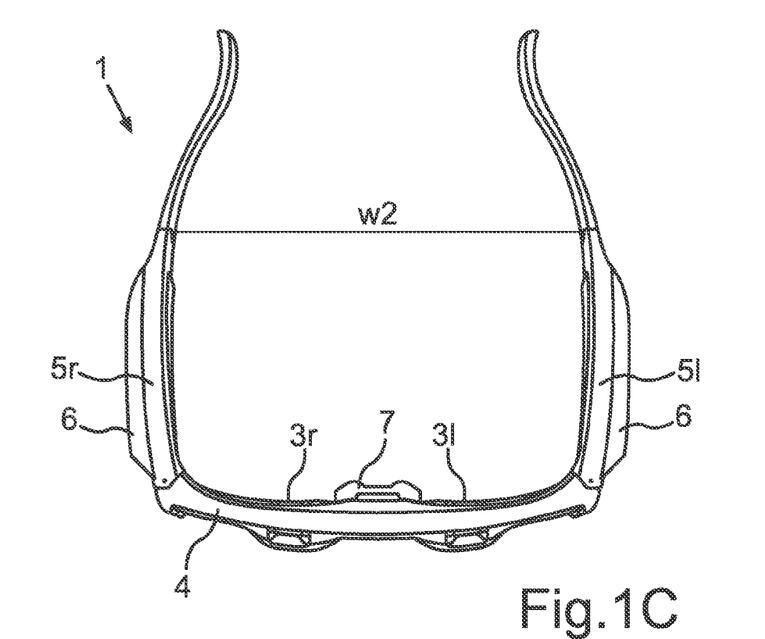
FIG. 1C a top view of the spectacle device of FIG. 1A.
Figure 1D:
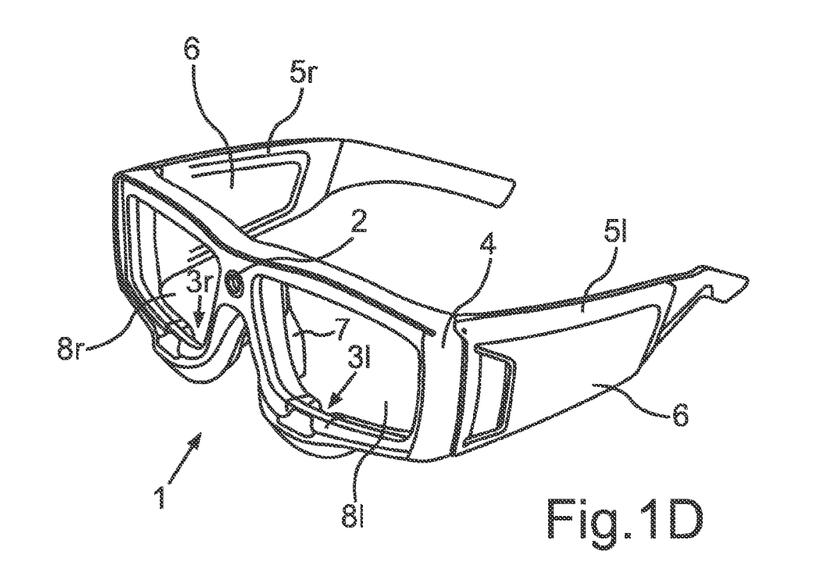
FIG. 1D a perspective view of the spectacle device of FIG. 1A.

FIGS. 1A to 1D show an optical measuring device which has the form of a spectacle device 1 or eye tracking device, respectively. The spectacle device 1 is designed such that a person can wear it on its head just like a normal pair of glasses. It comprises a frame 4 with two side bars 5*l* and 5*r* which support the spectacle device 1 on the ears of the person who is wearing it. Furthermore, the spectacle device 1 is held in place on the head by a nose support 7. The mainframe has a specific width w1 and height h. Its length l depends on the length of the sidebars 5*l* and 5*r*. As can be seen in FIG. 1C the sidebars 5*l* and 5*r* are hinged to the front part of the frame 4 such that the distance w2 between the side bars 5*l* and 5*r* can be enlarged or reduced (see dashed sidebar configuration for sidebar 5*l* in FIG. 1C).

Alternatively, the optical measuring device may not be designed in form of a regular pair of eye glasses, but may be designed such that it resembles a helmet, forming a frame, with a face shield, forming a frame insert.

Above the nose support 7 in the frame 4 a scene camera 2 is installed. It can either be attached to or integrated into the frame 4. With the scene camera 2 virtually a similar field of view can be captured as seen by a test person when wearing the spectacle device 1. In the lower part of the frame 4 the spectacle device 1 contains two eye cameras 3*l* and 3*r*. When the spectacle device 1 is worn by a person the person's eyes can be captured by the eye cameras 3*l* and 3*r*, which are integrated into the frame 4 at a suitable angle. Eye cameras 3*l* and 3*r* are designed to observe the person's left eye and right eye, respectively, i.e. capture characteristics of the person's eyes.

The frame 4 contains two openings which are filled with eye glass lenses 8*l* and 8*r* thus forming frame inserts. The pictures acquired by the scene camera 2 and the eye cameras 3*l* and 3*r* lead to signals which are processed in one or several pre-processing units 6 integrated into the sidebars 5*l* and 5*r*.

FIG. 2 shows an inside view of the spectacle device 1. Along the rim of the frame part enclosing the eye glass lenses 8*l* and 8*r* several Light Emitting Diodes (LEDs) 9 are located in a ring arrangement. When the spectacle device 1 is worn by a person, those LEDs 9 can illuminate the eyes of the test person in a defined way. The LEDs 9 will cause reflections on the eyes of the test person (cornea reflections) for all possible gaze angles. Those reflections can be detected by the eye cameras 3*l* and 3*r* and can be used for eye tracking.

The LEDs 9 can be switched on an off individually, in groups or all together following a specific time pattern, strobe characteristic or spatial variation. The on-off-switching-frequency of different LEDs 9 or groups of LEDs 9 may vary. Certain groups of LEDs 9 may get switched on exactly when other groups of LEDs 9 get switched off. A specific spatial and temporal correlation pattern may be implemented with regard to the switching and thus illumination characteristics. This way a reflection pattern can be created on the eyes that can be recognized easily by the eye cameras 3.

Figure 5:
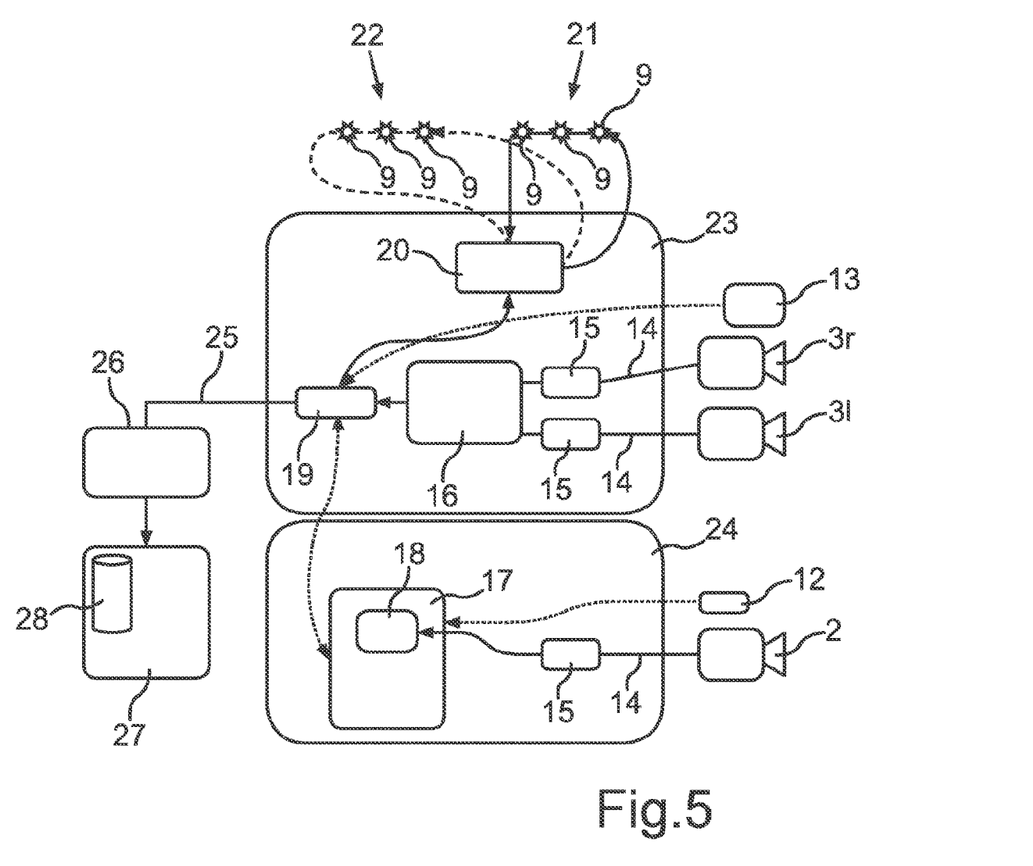
FIG. 5 a schematic view of individual electronic components comprised by a spectacle device.

The overall setup with the most important electronic components is shown in FIG. 5. The eye cameras 3*l* and 3*r* are connected to specific camera electronics 15 by 100 mm long cables 14. In particular, the cameras 3*l* and 3*r* comprise only basic electronic components while their major electronic components are located within the camera electronics 15. This way, the primarily "optical part" of the cameras 3*l* and 3*r* can be located remote to the primarily "electronic part" within the camera electronics 15. Both parts can then be connected by flex-PCB cables 14. This way, the optical sensor and the basic electronic components within the cameras 3*l* and 3*r* form a very small and highly compact entity while bulkier electronic components within the electronics 15 can be placed on more spacious integrated circuit boards elsewhere. The electronics 15 are connected to a pre-processing unit 16 which can process the signals from the eye cameras 3*l* and 3*r*. The pre-processing unit 16 can be identical to the pre-processing unit 6 located in the sidebars 5*l* and 5*r* of the spectacle device 1. The pre-processing unit 16 is connected to a USB-hub 19. The LEDs 9 installed in the frame 4 form a first and a second IR LED chain 21 and 22 arranged in a ring configuration around the eye glass lenses 8*l* and 8*r*. The IR LED chains 21 and 22 are connected to an IR LED constant current source 20, which is also connected to the USB-hub 19. The USB-hub 19 additionally serves as a power source for the IR LED constant current source 20. The LEDs 9 of the IR LED chains 21 and 22 can be switched on an off individually. To achieve this, they may be connected to the IR LED constant current source 20 in a parallel network with individual electrical switches for each LED 9 being implemented.

The USB-hub 19 is connected via a USB 2.0 cable 25 to a pre-processing unit 26. The signals pre-processed in the pre-processing unit 26 are finally analyzed in a personal computer 27, which contains a recorder device 28. An additional aux-/sync-port 13 forming an interface on the spectacle device 1 can also be connected to the USB-hub 19. The aux-/sync-port 13 can serve as interface for synchronization with other electronic devices or for triggering parallel data acquisitions. The electronics 15, preprocessing unit 16, USB-hub 19 and IR LED constant current source 20 are located on a common printed circuit board PCB 23.

In analogy to this setup the scene camera 2 is also connected to electronics 15 via a 100 mm cable 14. In this case the electronics 15 are located on a second printed circuit board PCB 24, which also contains a pre-processing unit 17. The pre-processing unit 17 can be based on electronics according to the DaVinci digital signal processor (DSP). It contains an MPEG encoder 18 for encoding the signals received from the electronics 15. A microphone 12 may also be connected to the pre-processing unit 17. The preprocessing unit 17 located on the PCB 24 is connected to the USB-hub 19. This way, processing signals acquired by the scene camera 2 are finally analyzed in the personal computer 27.

The pre-processing units 6, 16, 17 and 26 may be able to compress at least one of the three image streams generated by the two eye cameras 3l and 3r and the scene camera 2. Here, different alternatives are possible. A pre-processing unit may compress only the image stream of one camera while each camera has its own pre-processing unit. Alternatively, a single pre-processing unit may compress the image streams of all cameras. Furthermore, the pre-processing units may be configurable via a system interface and corresponding software to manage the bandwidth by adjustment of resolution, region of interest, frame rate and compression parameters. The pre-processing units may be designed to trigger synchronously the camera's image acquisition. They may provide time stamps for each acquired image which can be used to synchronise several or all camera data streams offline.

The pre-processing units may either be located on integrated circuit boards of the cameras or on a separate integrated circuit board that is located at or on a head mount (e.g. in the side bar 5l or 5r of the spectacle device 1) or in a separate housing that is worn by the test person 31, e.g. on a belt.

The spectacle device 1 may also comprise an auxiliary interface which allows to acquire data in real time from external sensors. Such sensors may be biometric sensors (including but not limited to EEG, ECG, etc.) or attitude sensors (including but not limited to accelerometers, magnetometers, gyroscopes, etc.). It is then possible to synchronise the data stream of the external sensors with the data streams acquired from the cameras 2, 3l and 3r. Furthermore, an external clock or trigger signal can be provided that can be used by the external sensors to synchronise themselves with the system. The bandwidth of data acquired from the interface can be reduced or compressed by means of on-board processing resources integrated in the system in its dedicated recording unit 28.

The eye cameras 3l and 3r can either be suited for visible or near infrared light. They are located symmetrically with respect to a vertical centre line that divides the user's face into two halves. The eye cameras 3l and 3r may be positioned in front and below the eyes 10l and 10r respectively, for example in or at the lower rim of a pair of eye glass lenses 8l and 8r, pointing at the eyes 10l and 10r in an angle of 30° to 50° and being mounted in the frame 4 in an angle of 30° to 50°. In the embodiment the eye cameras 3l and 3r are sensitive in the near infrared.

The scene camera 2 can be located on a vertical centre line that divides the user's face into two halves in or at the nose bridge of the frame 4. Alternatively, it may also be located at, in or close to the rim of a helmet, cap or headband. The scene camera 2 may have HD (high definition) and/or adjustable resolution of at least 720p (1280×720 pixels) and is operated at 30 Hz or 60 Hz. It can either be mounted in landscape or portrait orientation. Furthermore, it can be mounted such that its orientation can be changed from landscape to portrait orientation (camera roll) and also the direction the camera is pointing in (camera pan and tilt).

Instead of a single scene camera 2, the spectacle device 1 can also comprise a pair of scene cameras, where each scene camera can be oriented either in portrait mode or in landscape mode. Furthermore, each scene camera can be oriented independently of the respective second scene camera. Alternatively, both scene cameras 2 may have fixed orientations, which may or may not differ from each other.

Furthermore a prism or lens can be mounted in front of the scene camera 2 to create a different positioning of the field of view of the scene camera 2 with respect to the glasses, especially a more downward oriented field of view for near range reading applications.

Six LEDs 9 are located around each eyeglass lens 8. They emit in the infrared wavelength range (typically above 750 nm and below 1000 nm) at a central wavelength of 850 nm. They are driven by 50 mA current provided by the IR LED constant current source 20.

Instead of direct illumination of the eyes with the LEDs 9 also an implementation with a light guide can be envisaged. One or several segments of light guides (e.g. fiber optics) may be used. The illumination of the eyes may be implemented with focusing optics (structured illumination). Instead of the LEDs 9 suitable diffractive optics or lasers may be used to generate a pattern of coherent light for illuminating the eyes. The light source can be used together with an optical element in order to create a pattern of reflections on the eyes 10l and 10r (e.g. with focusing optics or diffractive optics). The illumination source may either emit visible or near infrared light. The illumination source may be positioned in or on the frame 4, in particular in a circle-like arrangement around the eye glass lenses 8l and 8r. Alternatively, the illumination source may be located on the rim or frame of a head mounted display. It may specifically be designed to create a pattern of reflections on the eye surfaces of the test person 31.

Figure 10A:
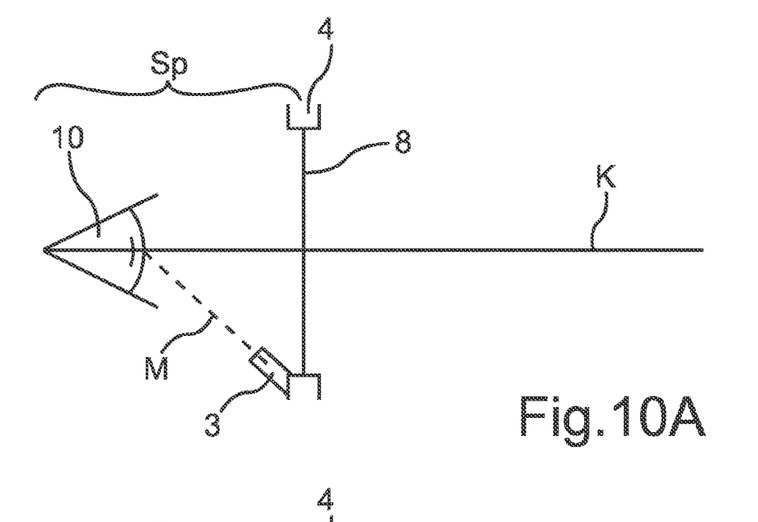
FIG. 10A a schematic side view of a spectacle device were the optical path of an eye camera extends in a straight line from the eye camera to an eye.

When the spectacle device 1 shown in FIG. 2 is worn by a test person the situation shown in FIG. 10A in a simplified way is realized. The eye camera 3 is arranged in such a way on the frame 4 that with the spectacle device 1 fixed to the head of a test person the optical path M capturing at least one parameter of the eye 10 extends in a straight line from the eye camera 3 to the eye 10.

Figure 10B:
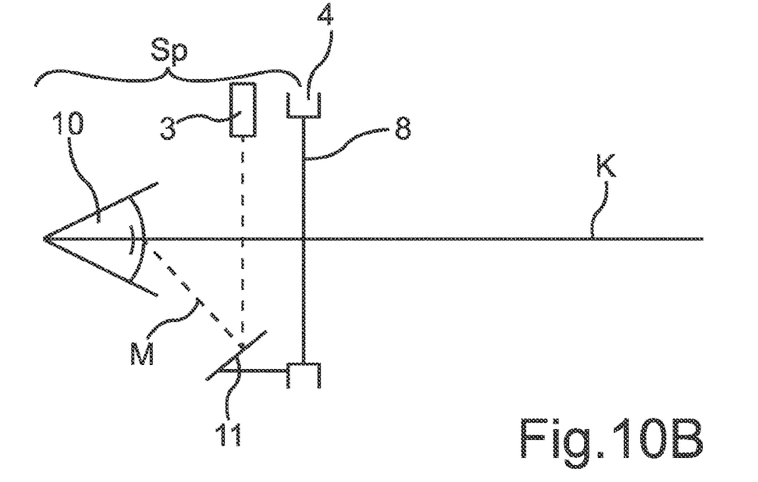
FIG. 10B a schematic side view of a spectacle device where the optical path of an eye camera extends from the eye camera via a mirror to the eye.

FIGS. 3 and 10B show a different configuration of the spectacle device 1. The spectacle device 1 comprises a mirror 11, forming an optical deflection element attached to the frame 4, the mirror 11 and the eye camera 3 being arranged in such a way on the frame 4 that with the spectacle device 1 fixed to the head of the test person the optical path M for capturing at least one parameter of the eye 10 extends from the eye camera 3 via the mirror 11 to the eye 10. The three dimensional representation of FIG. 3 shows the spectacle device 1 from a rear or inside view. In the figure, reflections of the left and right eye 10*l* and 10*r*, respectively, show in the eyeglass lenses 8*l* and 8*r*. The coordinate system is a Cartesian one with the z-axis being directed into the plane of projection.

Thus, the eye cameras 3*l* and 3*r* may be mounted in front of and above the eyes 10*l* and 10*r* with an optical guide or mirror 11 located in front and below the eyes 10*l* and 10*r*, for example in or at the lower rim of a pair of eye glass lenses 8*l* and 8*r* in order to acquire an image of each eye 10*l* and 10*r* from a forward and low perspective and to make that image visible to the eye cameras 10*l* and 10*r*. The optical guide or mirror 11 can either be a (flat) mirror, a spherical mirror, a dome, a custom lens, a holographic image guide, etc. The mirror 11 can be reflecting only a specific range of wavelength and be transparent to others.

The mirror 11 can either be a flat mirror or a spherical mirror. The advantage of a spherical mirror is that it magnifies the field of view of the eye camera 3 beyond the field of view achievable with a flat mirror. The configuration of FIG. 3 furthermore allows to place the optical system very close to the eye 10 (set direction) thus improving ergonomics and aesthetics. The test person's own field of view is hardly obstructed. The mirror 11 can be a so-called hot mirror, i.e. the mirror 11 is transparent in the visible wavelength range while having a higher reflectivity in the infrared wavelength range. It can be very thin and hollow (so-called dome) thus, minimizing the distortion due to refraction. It can be made out of a material showing a very low index of refraction (IOR).

In both cases (FIGS. 10A and 10B) the eye camera 3 is arranged in such a way that the optical path M for the capturing of at least one parameter of the eye 10 excludes the frame insert, i.e., the eye glass lens 8. Furthermore, the eye glass lens 8 is arranged in such a way that the optical axis K of the eye 10 and the optical path M as single jointly used optical element comprise the eye 10. Furthermore, the optical path M entirely runs within a space Sp which extends on the side of the eye glass lens 8 facing the eye 10.

The embodiments shown in FIGS. 2 and 3 and FIGS. 10A and 10B, respectively, both reduce eye occlusion due to the upper eye-lid.

Figure 6A:
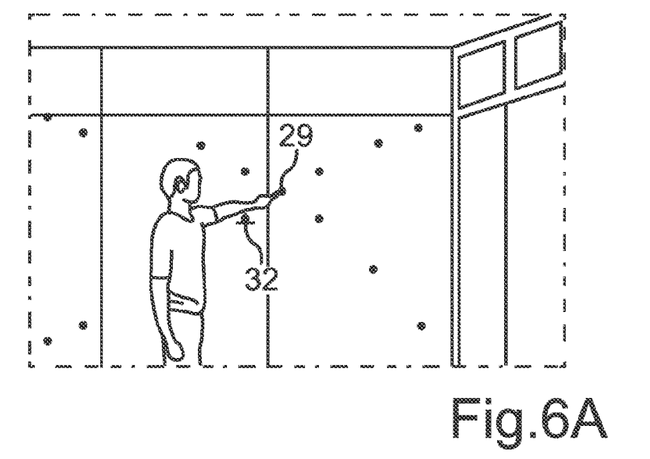
FIG. 6A a picture with a symbol indicating a large parallax error attained with an optical measuring device according to the prior art.
Figure 6B:
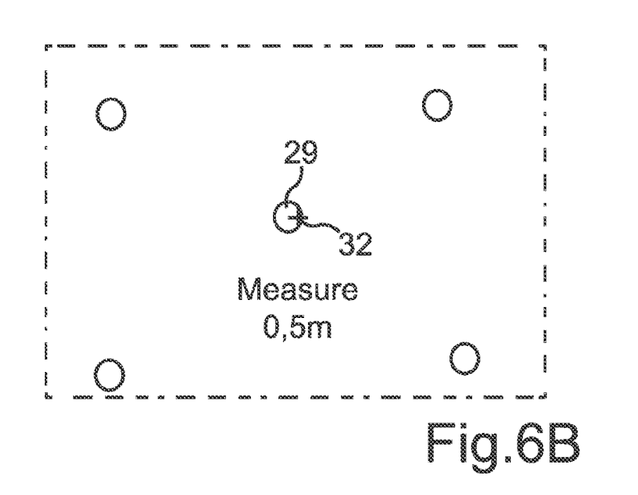
FIG. 6B a picture showing a symbol indicating the lack of a parallax error with a spectacle device according to an embodiment of the invention.

FIGS. 6A to 8 illustrate the reduction of parallax errors in the spectacle device 1 compared to the prior art. As can be seen in FIG. 6A the position of an object 29 the test person actually focuses its eyes on and the point of regard 32 determined by the spectacle device 1 usually do not coincide very well when using spectacle devices 1 as known from the prior art. This effect is usually the more pronounced the closer the test person is located to the object 29 that is to be focused. However, with the spectacle device 1 according to an embodiment of the invention the coincidence between the determined point of regard 32 and the actual object 29 is very good, even for measuring distances as low as 0.5 m (see FIG. 6B). This is achieved by minimizing the distance between the eye ball center and the camera focal point.

Figure 7:
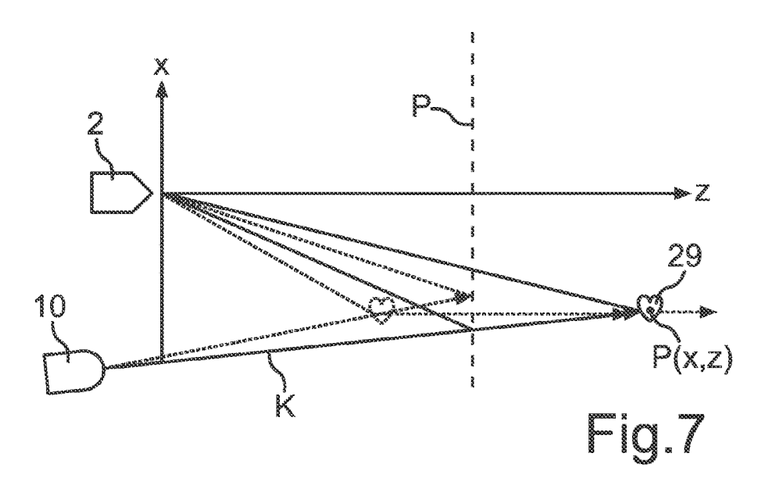
FIG. 7 a parallax error model.
Figure 8:
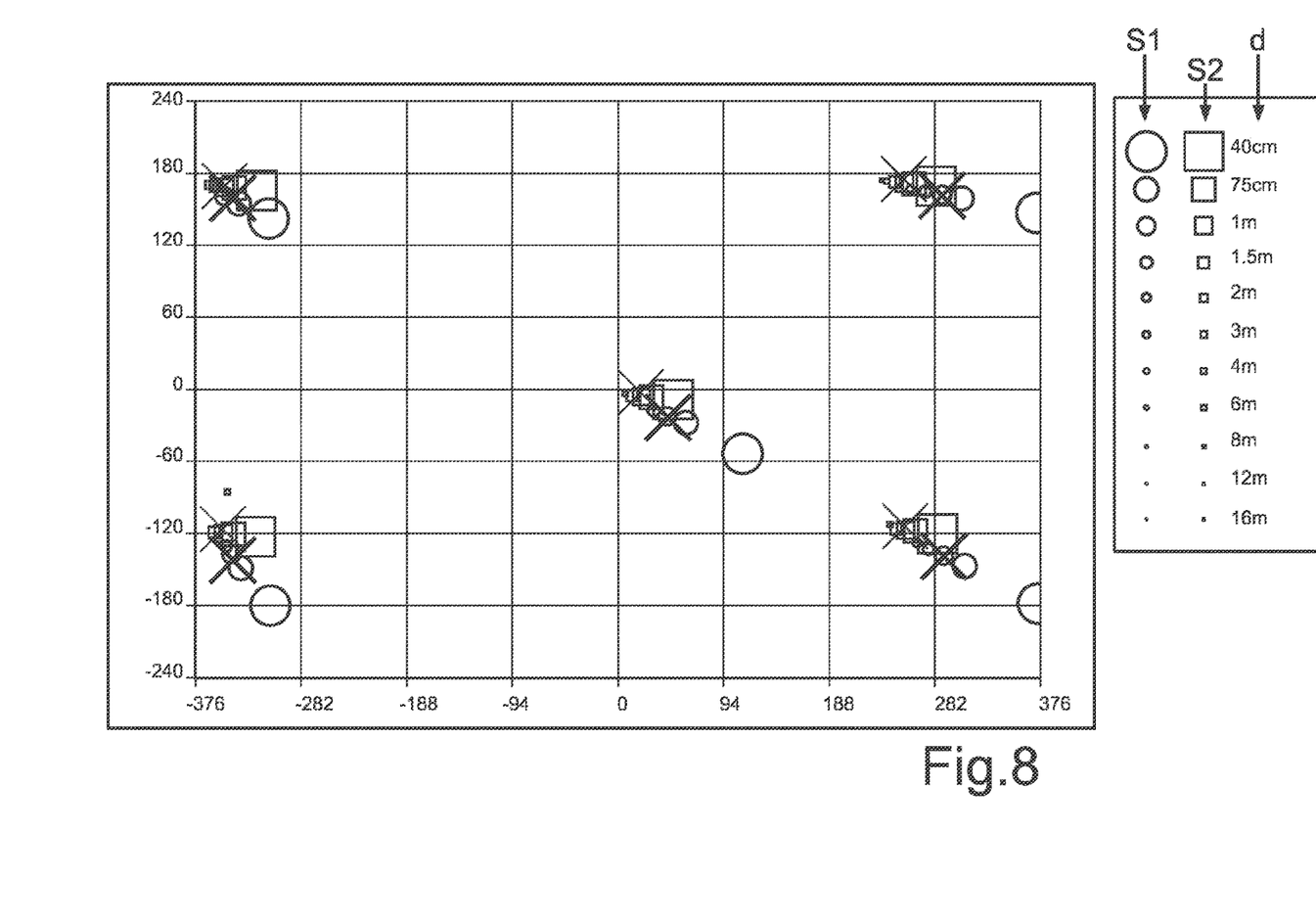
FIG. 8 a diagram comparing parallax errors of measuring devices according to the prior art and according to an embodiment of the invention.

The situation is again illustrated in FIG. 7. As eye 10 and scene camera 2 are located at slightly different positions the difference in their respective viewing angles for focussing the object 29 becomes the more pronounced the closer the object 29 is located to the eye 10 and scene camera 2, respectively (i.e. larger distortions for smaller z-values). The spectacle device 1 may get calibrated in the situation shown in FIG. 6B. The object 29 then lies in the calibration plain P and by calibrating the spectacle device 1 one can make sure that the determined point of regard 32 indeed falls onto the actual object 29. Calibration is typically performed on a plane at some distance from the test subject. It relates measured gaze direction (angles) to pixels in the scene video frame. This calculation gives valid results only for points that lie in that calibration plane. For points that do not lie on that plane, a systematic error (parallax) is introduced. When the distance of the spectacle device from the object 29 is increased the difference between the distance to the calibration plain P and the actual distance to the object 29 causes the pronounced deviations. With the spectacle device 1 according to an embodiment of the invention these deviations or parallax errors (indicated by symbols S2, circles, in FIG. 8) for all distances d are considerably smaller than with devices according to the prior art (symbols S1, rectangles). Thin-lined crosses relate to the group of symbols S2, while bold crosses relate to the group of symbols S1. The crosses correspond to the point of regard 32 used for calibration purposes.

The parallax error is mathematically modelled as a function of the position of the scene camera 2 with respect to the eye position. The gaze estimation error due to parallax is minimized by placing the scene camera 2 as close as possible to the eye 10, according to the results shown by the mathematical simulation. The parallax error can be further corrected by estimating the distance to the point of regard by using vergence from binocular tracking and by estimating the position of the eyes with respect to the eye tracking device.

Figure 9A:
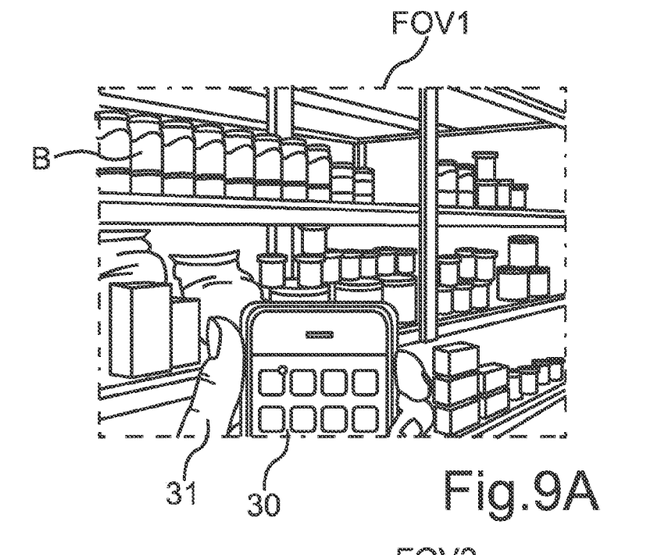
FIG. 9A a first field of view acquired by a scene camera.
Figure 9B:
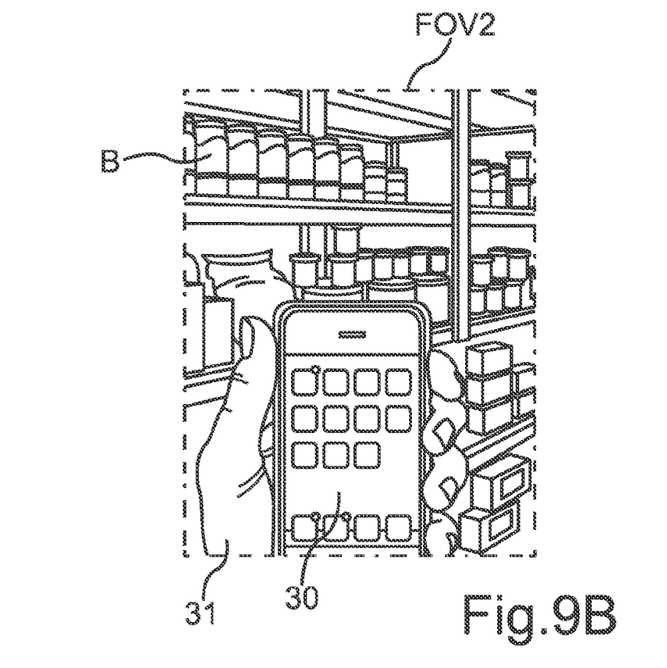
FIG. 9B a second field of view acquired by the scene camera.

To achieve even better results the field of view of the scene camera 2 can be optimized. The scene camera 2 with standard optics has a field of view that does not cover the full physiological gaze range (horizontal field of view of standard optics: 40° to 50°; typical physiological gaze range: 60°). In an embodiment the field of view of the scene camera 2 can thus be optimized depending on the respective application. One such field of view optimization method is illustrated in FIG. 9A and 9B. A user wearing the spectacle device 1 is at the same time observing a background B and his mobile phone 30. According to FIG. 9A the field of view FOV1 mainly covers the background B. When the test person 31 looks down onto its mobile phone 30 the change in gaze direction is automatically determined by the eye cameras 3*l* and 3*r* and the scene camera's 2 field of view is automatically adjusted by switching from landscape to portrait orientation (field of view FOV2). This can be achieved by a z-axis 90° mechanical roll of the scene camera 2 or by the use of an optical prism in front of the scene camera 2. Also the use of two scene cameras with different tilt or roll angles is possible. Alternatively, also an optical beam splitter may be used in front of the scene camera 2.

In summary, the spectacle device 1 forms a head-mounted eye tracking system which consists of three cameras: two eye cameras 3*l* and 3*r* and at least one scene camera 2. The three cameras 3*l*, 3*r* and 2 can have a manageable bandwidth, for example by adjustable frame rates or resolutions. One or several pre-processing units 6, 16, 17 and 26 may exist that perform variable compression of the video streams received from the cameras 2, 3*l* and 3*r*. The level of compression of the video streams may be the same for the eye cameras 3*l* and 3*r* and the scene camera 2, or the video streams may be separately compressed for the eye cameras 3*l* and 3*r* and the scene camera 2. The frame rate for eye camera 3*l* may correspond to full speed acquisition, the one of eye camera 3*r* may correspond to $\frac{1}{10}$ speed acquisition and the one for the scene camera 2 may correspond to $\frac{1}{2}$ speed acquisition. Instead of adjusting the frame rates of the different cameras, alternatively the acquisition rates may be chosen to be the same, while data processing is performed differently for each camera. Data provided by one camera may be compressed more than data provided by another camera, although both cameras acquire the same amount of data. One may also combine different compression rates with different acquisition rates. It is also possible to omit, for example, every second acquired image when transferring the data and thus reduce the amount of data to be sent to the CPU by half. The signals of the cameras 2, 3l and 3r may be transferred to a CPU in the PC 27 via a wired or wireless interface (see FIG. 5). Auxiliary interfaces for other data sources and methods for synchronisation with these data sources may be implemented in the spectacle device 1.

The spectacle device 1 can come as a system comprising several exchangeable pieces. The spectacle device 1 can have an exchangeable set of nose pieces or nose supports 7 for faces with small or large noses. This way, the spectacle device 1 can be worn over vision correction glasses without a problem. Furthermore, the spectacle device 1 has a holding mechanism for exchangeable glasses that can have different levels of light transmittance (e g. clear glasses or sun glasses) for a certain range of wavelengths. Additionally or alternatively the exchangeable glasses can have a near infrared optical filter to match the wavelength of the illumination source and block some or all light from the outside of same and similar wavelengths from reaching the eye surface to improve signal to noise on the eye surface. The spectacle device 1 has rims and a nose bridge that serve as a mount or housing for the eye cameras 3l and 3r and the scene camera 2. The eye cameras 3l and 3r are mounted in such a way that their field of view extends behind the exchangeable glasses 8l and 8r.

With the spectacle device 1 it is possible to do eye tracking, occulometrics, biometrics and position and motion measurements in order to measure and classify as fully as possible human behaviour in a free range movement setup. A head mounted eye tracking device is realised which is calibration-free and provides an astigmatism estimation. The eye-tracking functionality has zero set-up time. No adjustments are necessary. A test person 31 can just put the spectacle device 1 on and start using it. It has a very large gaze-tracking range covering the physiological range of human eye movement (80° horizontal, 60° vertical). It is very robust and has a high accuracy in gaze mapping. Astigmatism is compensated for, parallax is minimized, pupil axis shift is compensated and the device is calibration free or can be calibrated using a one-point calibration feature. Furthermore, it is designed to work irrespective of ethnic group (Caucasian, Asian, African, etc.), gender and age. The field of view of the scene camera 2 is optimized. By the use of optical, inertial or magnetic sensors a head tracking functionality can be implemented. The spectacle device furthermore offers biometric features, such as measuring the pupil or limbus diameter and offering interfacing and synchronisation options with EEG, ECG, EOG etc. Finally, it can be integrated with a head mounted display. It is possible to project a virtual image onto a subject's eye of a portable computer screen. Furthermore, the possibility is offered to interact with "objects" in the virtual image using eye movement (gaze, blinks).

Head tracking functionality can be realized by the use of three axis gyroscopes, three axis accelerometers and/or three axis magnetometers with optional sensor fusion for six dimensional head tracking.

In summary, the spectacle device 1 offers a very specific optical and electronic architecture. With respect to the electronic architecture three or more high resolution cameras with allocateable bandwidth are incorporated in the device 1. Separate processing channels for eye cameras 3l and 3r and the scene camera 2 are envisaged. The optical architecture is characterized by exchangeable glasses with various properties. The optical path of the eye cameras 3l and 3r extends behind the glasses or eye glass lenses 8l and 8r respectively. Furthermore, a set of LEDs 9 allows for highly variable illumination of the eyes 10l and 10r. For instance, the illumination geometry around the eye can be controlled. The specific LED subsets can be controlled with regard to strobe effect and sequencing. Finally, eye illumination can be achieved by point, line or two-dimensional light sources.

REFERENCE SIGNS 1 spectacle device
2 scene camera
3, 3l, 3r eye camera
4 frame
5l, 5r side bar
6 pre-processing unit
7 nose support
8, 8l, 8r eyeglass lens
9 LED
10, 10l, 10r eye
11 mirror
12 microphone
13 aux-/sync-port
14 cable
15 electronics
16 pre-processing unit
17 pre-processing unit
18 MPEG encoder
19 USB hub
20 IR LED constant current source
21, 22 IR LED chain
23, 24 PCB
25 USB 2.0 cable
26 pre-processing unit
27 PC
28 recorder
29 object
30 mobile phone
31 test person
32 point of regard
w1, w2 width
h height
l length
a tilt angle
K optical axis
M optical path
O origin of system of reference
P calibration plane
Sp space
d distance
S1, S2 symbols
B background
FOV1, FOV2 field of view
x, y, z axis

The invention claimed is:
1. An optical measuring device for capturing at least one parameter of at least one eye of a test person wearing the optical measuring device, comprising:
a frame,
at least one frame insert attached to the frame, and
at least one capturing unit,
wherein the frame is designed to fix the optical measuring device in such a way to the head of the test person, that the at least one frame insert is positioned in front of at least one eye of the test person for at least one direction of view of the at least one eye on the optical axis of the at least one eye,
wherein the capturing unit is designed to optically capture the at least one parameter of the at least one eye, and is arranged in such a way that the optical path for the capturing of the at least one parameter of the at least one eye excludes the frame insert, and
wherein the frame insert is arranged in such a way that, with the optical measuring device fixed to the head of the test person, through a connection line of a point of the frame insert with the eye of the test person a view path is determined and the capturing unit arranged in such a way that the optical path for capturing the at least one parameter of the eye and the view path as a sole jointly used optical element comprise the eye.

2. The optical measuring device according to claim 1, wherein the optical path entirely runs within a space which, with the optical measuring device fixed to the head of the test person, extends on the side of the frame insert facing the at least one eye.

3. The optical measuring device according to claim 1, wherein the at least one frame insert has at least one optical property.

4. The optical measuring device according to claim 3, wherein the at least one frame insert is configured as an optical element, including an optical lens and/or a diffractive optical element.

5. The optical measuring device according to claim 3, wherein the at least one frame insert is configured as optical spectral filter, having a highpass filter, lowpass filter, bandpass filter, or notch filter.

6. The optical measuring device according to claim 1, wherein the capturing unit, at least in one pre-determinable spectral range, is optically sensitive.

7. The optical measuring device according to claim 6, further comprising:
at least one illumination unit which, with the optical measuring device fixed to the head of the test person, is configured to emit radiation in the pre-determinable spectral range in such a way that the radiation at least partly hits the at least one eye.

8. The optical measuring device according to claim 6, wherein the at least one frame insert in the pre-determinable spectral range has a transmittance of at most 50%, preferentially less than 20%.

9. The optical measuring device according to claim 6, wherein the pre-determinable spectral range is in the infrared wavelength range.

10. The optical measuring device according to claim 1, wherein the capturing unit comprises at least one camera and is arranged in such a way on the frame that, with the optical measuring device fixed to the head of the test person, the optical path capturing the at least one parameter of the at least one eye extends in a straight line from the camera to the eye.

11. The optical measuring device according to claim 1, further comprising:
an optical deflection element, with the optical deflection element and the capturing unit being arranged in such a way on the frame that, with the optical measuring device fixed to the head of the test person, the optical path for capturing the at least one parameter of the at least one eye extends from the capturing unit via the deflection element to the eye,
wherein the part of the optical path for capturing the at least one parameter of the at least one eye that extends from the deflection element to the eye extends in a straight line from the deflection element to the eye, and
wherein the deflection element is spatially separated from the frame insert.

12. The optical measuring device according to claim 1, wherein the at least one captured parameter concerns (i) an orientation, or (ii) a position, or (iii) an eyelid closure, or (iv) a pupil diameter, or (v) a sclera characteristic, or (vi) an iris characteristic, or (vii) a characteristic of a blood vessel, or (viii) a cornea characteristic of the at least one eye.

13. The optical measuring device according to claim 1, wherein the frame insert comprises a display unit, disposed such that, with the optical measuring device fixed to the head of the test person, a display on the display unit is optically capturable by the at least one eye of the test person.

14. A system comprising an optical measuring device according to claim 1 and at least two frame inserts which differ in their transmission and/or reflection properties, wherein the frame is configured in such a way that the at least two frame inserts are exchangeably attachable to it.

15. An optical measuring device for capturing at least one parameter of at least one eye of a test person wearing the optical measuring device , comprising:
a frame,
at least one frame insert attached to the frame, and
at least one capturing unit,
wherein the frame is designed to fix the optical measuring device in such a way to the head of the test person, that the at least one frame insert is positioned in front of at least one eye of the test person for at least one direction of view of the at least one eye on the optical axis of the at least one eye,
wherein the capturing unit (i) is designed to optically capture the at least one parameter of the at least one eye, and (ii) is arranged in such a way that the optical path for the capturing of the at least one parameter of the at least one eye excludes the frame insert,
wherein the frame insert is configured as a display unit such that, with the optical measuring device fixed to the head of the test person, a display on the display unit is optically capturable by the at least one eye of the test person.

16. An optical measuring device for capturing at least one parameter of at least one eye of a test person wearing the optical measuring device, comprising:
a frame,
at least one frame insert attached to the frame, and
at least one capturing unit,
wherein the frame is designed to fix the optical measuring device in such a way to the head of the test person, that the at least one frame insert is positioned in front of at least one eye of the test person for at least one direction of view of the at least one eye on the optical axis of the at least one eye,
wherein the capturing unit is (i) designed to optically capture the at least one parameter of the at least one eye, and (ii) is arranged in such a way that the optical path for the capturing of the at least one parameter of the at least one eye excludes the frame insert, and
wherein the at least one frame insert is configured as one or both of an optical lens and a diffractive optical element, or is configured as an optical spectral filter.

17. The optical measuring device according to claim 16, wherein the at least one frame insert is configured as an optical spectral filter.

* * * * *